United States Patent [19]

Bernhardt et al.

[11] Patent Number: 4,927,948

[45] Date of Patent: May 22, 1990

[54] PROCESS FOR STABILIZING ORGANOSILANES CONTAINING METHACRYLOXY OR ACRYLOXY GROUPS

[75] Inventors: Günther Bernhardt, Sankt Augustin; Jürgen Amort; Heinz Kragl, both of Troisdorf; Margret Haas, Cologne, all of Fed. Rep. of Germany

[73] Assignee: Huels Aktiengesellschaft, Troisdorf, Fed. Rep. of Germany

[21] Appl. No.: 409,604

[22] Filed: Sep. 19, 1989

[30] Foreign Application Priority Data

Sep. 26, 1988 [DE] Fed. Rep. of Germany ....... 3832621

[51] Int. Cl.$^5$ ............................ C07F 7/08; C07F 7/18
[52] U.S. Cl. .................................................. 556/401
[58] Field of Search .......................................... 556/401

[56] References Cited

U.S. PATENT DOCUMENTS

| | | | |
|---|---|---|---|
| 2,389,802 | 11/1945 | McGregor et al. | 556/401 |
| 2,389,803 | 11/1945 | McGregor et al. | 556/401 |
| 2,517,536 | 8/1950 | Chenicek | 556/401 |
| 2,697,114 | 12/1954 | Chenicek | 556/401 |
| 3,816,267 | 6/1974 | Chuang | 556/401 X |
| 4,754,046 | 6/1988 | Nevis | 556/401 |
| 4,780,555 | 10/1988 | Bank | 556/401 X |
| 4,798,889 | 1/1989 | Plueddemann et al. | 556/401 |

FOREIGN PATENT DOCUMENTS 0736504  6/1966  Canada ................................ 556/401

*Primary Examiner*—Paul F. Shaver
*Attorney, Agent, or Firm*—Felfe & Lynch

[57] ABSTRACT

Organosilanes comprising methacryloxy groups or acryloxy groups are stabilized with a mixture consisting of at least one N,N'-di-substituted-p-phenylenediamine and at least one substituted phenol, which yields products with high purity and high yields.

3 Claims, No Drawings

PROCESS FOR STABILIZING ORGANOSILANES CONTAINING METHACRYLOXY OR ACRYLOXY GROUPS

Field of the Invention

This invention relates to a novel method of stabilizing organosilanes containing methacryloxy or acryloxy groups of the formula

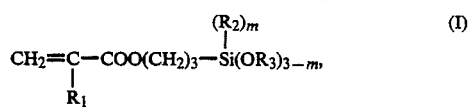

wherein $R_1$ is hydrogen or methyl, $R_2$ and $R_3$, which may be identical to or different from each other, are each independently alkyl of 1 to 4 carbon atoms, and m is 0, 1 or 2.

These silanes are hereinafter also referred to as acrylsilanes.

BACKGROUND OF THE INVENTION AND THE PRIOR ART

Various different methods for the preparation of acrylsilanes are known. Thus, U.S. Pat. No. 3,258,477 discloses that acrylsilanes can be prepared by subjecting trialkoxysilanes to an addition reaction with allylacrylate or allylmethacrylate in the presence of platinum-containing catalysts. This method yields contaminated and discolored raw products which cannot be used for technical purposes as such. Especially acrylsilanes which are to be used for the manufacture of polymerizates require a high degree of purity and colorless appearance.

In order to separate acrylsilanes from the crude reaction mixtures, distillation, preferably under reduced pressure, is exclusively used. To avoid polymerization or gel formation during distillation, a number of stabilizers have been suggested, for example, p-benzoquinone, hydroquinone, 2.5-di-tert, butyl-beuzoquinone p-methoxyphenol or 2.5-di-tert.butyl-hydroquinone (see German Pat. No. 511 83 503 and 2,238,295 as well as European published application 0,162,390. However, when acrylsilanes are to be distilled, the stabilizing effect of the known stabilizers is either inadequate, or they cause the distillate to be discolored.

Additional stabilizers which have been proposed are N,N'-disubstituted p-phenylenediamines; such as N,N'-diphenyl-p-phenylenediamine, or sterically hindered phenols. These stabilizers, however, do not meet the requirements either which are expected of a good stabilizer. Thus, the use of substituted p-phenylenediamines causes polymerization in the sump to be substantially suppressed, but in the vapor phase the formation of "popcorn"-polymerizates occurs during distillation, which can lead to stoppages in the distillation columns, pipe systems or cooling system and can give rise to significant operational interruptions.

The use of substituted or sterically hindered phenols reduces the formation of "popcorn"-structures, but the formation of polymerizate in the sump is considerable unless very large amounts of these phenols are used. However, since these phenols pass over with the acrylsilanes during distillation, their proportion in the distillate is correspondingly high, which produces significant difficulties if these acrylsilanes are used for the preparation of polymerizates, because the phenols significantly inhibit or entirely suppress the polymerization.

European Pat. No. 0 247 501 discloses the preparation of acrylsilanes in the presence of phenolic stabilizers, aromatic amines or combinations of these. In this method, however, there is also the danger of gel formation.

OBJECT OF THE INVENTION

It is an object of the present invention to provide stabilizers for acrylsilanes which prevent polymerization during the distillation in the sump phase as well as in the vapor phase and additionally do not produce discoloration of the distillate.

Other objects and advantages of the present invention will become apparent as the description thereof proceeds.

DESCRIPTION OF THE INVENTION

The above object is achieved in accordance with the instant invention by providing method for stabilizing of acrylsilanes which comprises using as stabilizers a mixture consisting of (a) one or more N,N'-di-substituted p-phenylenediamines of the formula

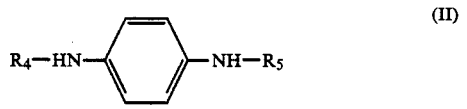

wherein $R_4$ and $R_5$, which may be identical to or different from each other, are each individually phenyl, naphthyl, straight or branched alkyl of 3 to 8 carbon atoms, or cyclohexyl, and (b) one or more substituted phenols of the formula

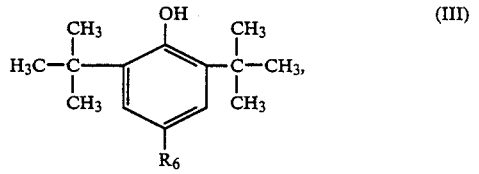

wherein $R_6$ is alkyl of 1 to 4 carbon atoms or alkoxy of 1 to 4 carbon atoms.

Examples of N,N'-di-substituted p-phenylenediamines of the formula II are:
N,N'-diphenyl-p-phenylenediamine,
N,N'-dinaphthyl-p-phenylenediamine,
N,N'-di-(1-methylheptyl)-p-phenylenediamine,
N,N'-di-(1-ethyl-3-methylpentyl)-p-phenylenediamine,
N,N'-di-(1,4-dimethylpentyl)-p-phenylenediamine,
N,N'-di-sec.butyl-p-phenylenediamine,
N-phenyl-N'-cyclohexyl-p-phenylenediamine and
N-phenyl-N'-isopropyl-p-phenylenediamine.

Examples of substituted phenols of the formula III are:
2,6-di-tert.butyl-4-methylphenol,
2,6-di-tert.butyl-4-ethylphenol and
2,6-di-tert.butyl-4-methoxyphenol.

The stabilizer combinations pursuant to the present invention, that is, the combination of compounds of the formulas II and III may already be present during the preparation of the acrylsilanes, or they may be added just before or in the course of the distillation.

It is also possible, however, that neither or optionally only one component of the combination pursuant to the present invention is present during the preparation of the acrylsilanes and that the stabilizer combination is added or completed only at the beginning or during the course of the distillation.

Several of the compounds of the formulas II and III may be contained in the stabilizer combination. It is preferred, however, that only one compound of the formulas II and III, respectively, is present.

The compounds of the formula II are preferably used in amounts of 0.01 to 5 weight-%, and the compounds of the formula III are preferably used in amounts of 0.001 to 1 weight-%, each based on the amount of acrylsilane.

The presence of oxygen, for instance in the form of air, can be of advantage during the distillation.

The presence of auxiliary agents, which are required for the preparation of the acrylsilanes, such as catalysts or solvents, does not adversely affect the action of the stabilizers, provided they are not chemically altered by the auxiliary agents.

The known shortcomings in connection with the distillation of acrylsilanes are eliminated by using the stabilizer combination in accordance with the present invention. The formation of "popcorn"-polymerizates in the vapor phase is eliminated, and the formation of polymerizate in the sump phase is kept to a minimum. The distillates are not discolored and meet the highest standards of the lacquer industry. Thus, in comparison to known methods, the method of the instant invention produces higher yields and products of the highest purity.

The following examples illustrate the present invention and will enable others skilled in the art to understand it more completely. It should be understood, however, that the invention is not limited solely to the particular examples given below.

EXAMPLE 1

A mixture of 0.5 liter of toluene, 24.4 g (0.2 mol) of trimethoxysilane and 1.05 g of a 10 weight-% solution of $H_2PtCl_6$ in acetone was heated to 105° C., and an additional mixture of 219.6 g (1.8 mols) of trimethoxysilane, 252 g (2 mols) of allylmethacrylate and 3 g of 2,6-di-tert.butyl-4-methoxyphenol was added thereto over a period of 2 hours, during which time the temperature was maintained between 100° and 105° C. Thereafter, the mixture was heated at 110° C. for a further hour. The low boiling point components were distilled off, toward the end under a mild vacuum. After addition of 4.5g of N-phenyl-N'- cyclohexyl-p-phenylenediamine, the residue was distilled under reduced pressure by way of a short packed column, whereby 396.8 g of 3-methacryloxypropyl-trimethoxysilane passed over as the main fraction at 110° to 112° C. (3 mbars), which corresponds to a yield of 80%, based on the amount of allylmethacrylate originally used. There is no "popcorn"-polymerizate in the column, the distillation residue is a thin liquid, and the distillate has a Hazen number of less than 10.

EXAMPLE 2

A mixture of 189.0g (1.5mols) of allylmethacrylate, 0.6ml of a 10 weight-% solution of $H_2PtCl_6$ in acetone, 0.1g of 2,6-di- tert.butyl-4-methylphenol and 1.2 g of N,N'-diphenyl-pphenylenediamine was heated to 60° C. while stirring, and was admixed with 189.1g (1.55mols) of trimethoxysilane over a period of 30 minutes, the reaction mixture temperature being kept between 70 and 80° C. by cooling. The low boiling point components were subsequently distilled out, toward the end under a mild vacuum. The residue was distilled under reduced pressure by way of a short packed column, whereby 302.1g of 3-methacryloxypropyltrimethoxysilane passed over as the main fraction at 78° to 79° C. (0.3mbar), which corresponds to a yield of 81.2%, based on the amount of allylmethacrylate originally used. There is no "popcorn"-polymerizate in the column, the distillation residue is a thin liquid, and the distillate has a Hazen number of less than 10.

EXAMPLE 3

Example 2 was repeated, except that 0.15 g of 2,6-di-tert.butyl-4-ethylphenol and 2.2 g of di-2-naphthyl-p-phenylenediamine were used in place of 2,6-di-tert.butyl-4methylphenol and N,N'-diphenyl-p-phenylenediamine. 299.8 g of distilled 3-methacryloxypropyl-trimethoxysilane were obtained, which corresponded to a yield of 80.6%, based on the amount of allylmethacrylate originally used. The column was free of "popcorn"-polymerizate, and the distillation residue was liquid. The Hazen number of the distillate was less than 10.

COMPARATIVE EXAMPLE A

Example 2 was repeated except that no 2,6-di-tert.-butyl-4-methylphenol was added. During the course of the distillation a significant amount of "popcorn"-polymerizate formed in the packed column, which caused the column to be blocked. The distillation residue had a gel-like consistency.

COMPARATIVE EXAMPLE B

Example 2 was repeated, except that N,N'-diphenyl-p-phenylenediamine was not used. In the course of the distillation, polymerization occurred in the sump. More than half of the starting product had solidified into a gel and was very difficult to remove from the distillation flask.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of stabilizing organosilanes containing methacryloxy groups or acryloxy groups of the formula

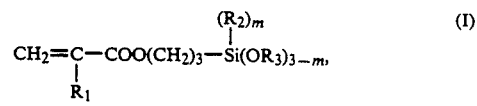

wherein R1 is hydrogen or methyl,
R2 and R3, which may be identical to or different from each other, are each individually alkyl of 1 to 4 carbon atoms, and
m is 0, 1 or 2, which comprises using as a stabilizer a mixture comprising
(a) at least one N,N'-di-substituted-p-phenylenediamine of the formula

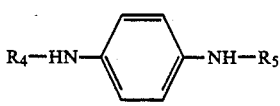

(II)

wherein T4 and R5, which may be identical to or different from each other, are each individually phenyl, naphthyl, straight or branched alkyl of 3 to 8 carbon atoms or cyclohexyl, and (b) at least one substituted phenol of the formula

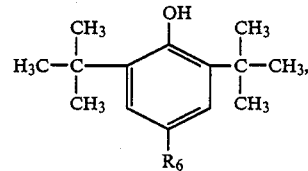

(III)

wherein $R_6$ is alkyl of 1 to 4 carbon atoms or alkoxy of 1 to 4 carbon atoms.

2. The method of claim 1, wherein said mixture contains 0.01 to 5 weight-% of compounds of the formula II, and 0.001 to 1 weight-% of compounds of the formula III, each based upon the amount of organosilane.

3. The method of claim 1, wherein the stabilizer mixture consists of N,N'-diphenyl-p-phenylenediamine and 2,6-di- tert.butyl-4-methylphenol.

* * * * *

UNITED STATES PATENT AND TRADEMARK OFFICE
CERTIFICATE OF CORRECTION

PATENT NO.  : 4,927,948
DATED       : May 22, 1990
INVENTOR(S) : Günther Bernhardt et al It is certified that error appears in the above-identified patent and that said Letters Patent is hereby corrected as shown below:

Column 1, lines 42 and 43, "2.5" should read --2,5--.

Column 1, line 44, "Pat. No." should read --Patents--.

Column 3, line 54, "3-metha" should read --$\gamma$-metha--.

Column 5, line 11, "$T_4$" should read --$R_4$--.

Signed and Sealed this

Twenty-third Day of April, 1991

Attest:

HARRY F. MANBECK, JR.

*Attesting Officer*    *Commissioner of Patents and Trademarks*